United States Patent [19]

Mersky

[11] Patent Number: 5,033,999
[45] Date of Patent: Jul. 23, 1991

[54] METHOD AND APPARATUS FOR ENDODONTICALLY AUGMENTING HEARING

[76] Inventor: Barry L. Mersky, 7315 Wisconsin Ave. #607 W., Bethesda, Md. 20814

[21] Appl. No.: 426,176

[22] Filed: Oct. 25, 1989

[51] Int. Cl.⁵ ............................................ H04R 25/00
[52] U.S. Cl. ...................................... 600/25; 381/68.3
[58] Field of Search .......................... 128/746; 600/25; 379/52; 381/68.3, 151; 433/201.1; 181/127, 128

[56] References Cited

U.S. PATENT DOCUMENTS

| | | |
|---|---|---|
| 2,161,169 | 6/1939 | Jefferis, Jr. ........................... 433/167 |
| 2,995,633 | 8/1961 | Puharich et al. ...................... 600/25 |
| 4,498,461 | 2/1985 | Hakansson ............................ 600/25 |

Primary Examiner—William E. Kamm
Assistant Examiner—Kevin Pontius
Attorney, Agent, or Firm—Epstein, Edell & Retzel

[57] ABSTRACT

An audiodontic device includes a transducer implanted in a dental post hole drilled into a root canal of a tooth, preferably a maxillary molar. The transducer imparts vibratory signals to the tooth in response to applied audio signals. A precision attachment device includes a female connector embedded in a dental crown of electrically non-conductive material covering a built-up core and through which electrical leads, or the like, extend to transducer terminals located at the core periphery. Audio signals are delivered to the transducer from a radio receiver or induction loop embedded in an insulative housing contoured for buccal or lingual vestibular mounting adjacent the tooth, or disposed in a denture or retainer. In either case, a male connector for the precision attachment conducts the received audio signal from the receiver to the tooth. The female connector includes a channel contoured to slidably receive the male connector to thereby firmly hold the receiver housing in place while maintaining the necessary electrical contact to pass the received audio signal to the transducer.

21 Claims, 2 Drawing Sheets

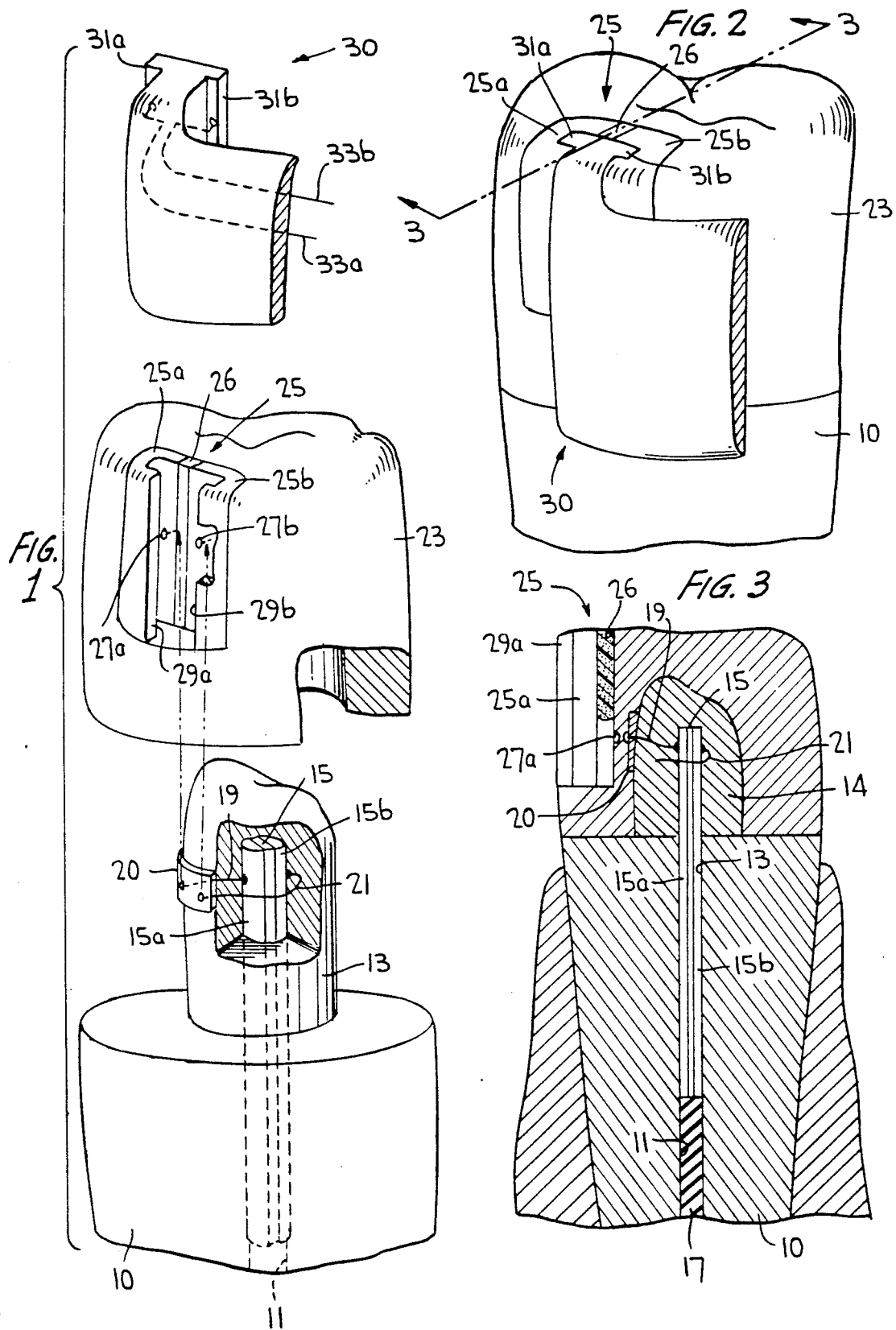

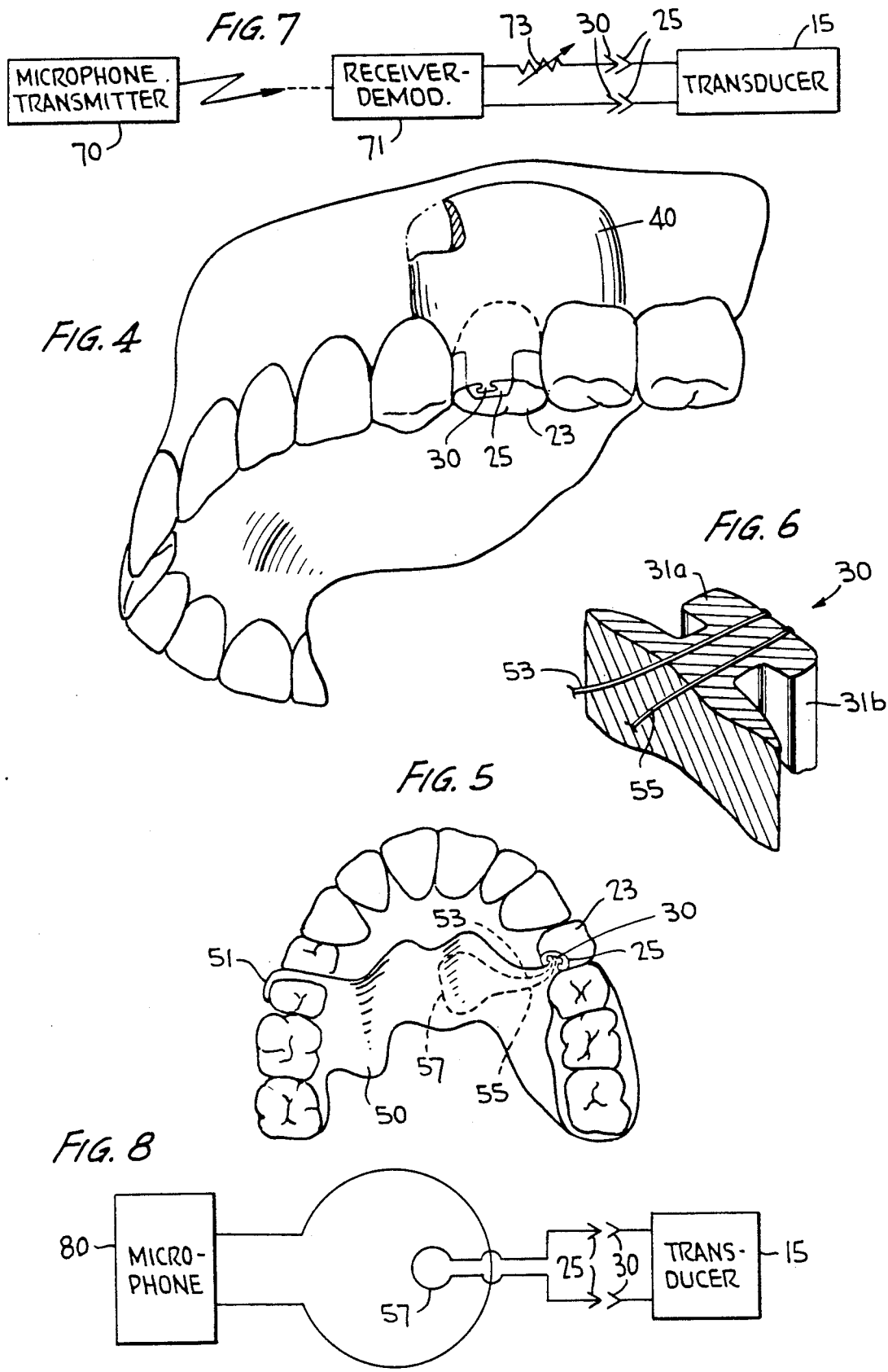

METHOD AND APPARATUS FOR ENDODONTICALLY AUGMENTING HEARING

BACKGROUND OF THE INVENTION

1. Technical Field

The present invention relates to methods and apparatus for augmenting hearing and, more particularly, to improvements in hearing aids of the type wherein acoustic vibrations are transmitted to the ear via bone structure.

2. Discussion of the Prior Art

It is known in the prior art that certain hearing impaired persons experience significantly improved hearing function when provided with devices that operate to convert sound to mechanical vibrations that are applied to bones in the skull. These vibrations ultimately stimulate the cochlea, resulting in a perception of sound. For examples of such devices, reference is made to the discussion in U.S. Pat. No. 4,606,329 (Hough). See also, U.S. Pat. Nos. 4,612,915 (Hough et al) and 4,774,933 (Hough et al). These patents describe prior art bone conduction devices and are primarily concerned with prostheses that are surgically embedded into the mastoid or temporal bone. The express purpose of the technique is to have the prosthetic device integrate into bone tissue so that it may thereafter be used as a source of vibrations that ultimately stimulate the cochlea. Although the technique has merit, in practice it has a number of disadvantages. For example, all tissue-integrated prostheses must be selectively utilized in order to preclude an unacceptably high failure rate, thereby severely limiting the population for whom the technique is available. In addition, there is a real risk of infection developing from tissue-integrated prosthetic devices; in this regard, a middle ear infection can result in the occurrence of life-threatening mastoiditis or meningitis. Further, from a cosmetic perspective, the prosthetic device requires a very evident supercutaneously mounted transducer for converting sound waves to electrical audio signals. Finally, implantation of the prosthetic device involves invasive surgical procedures that must be performed by specially trained otolaryngologists.

In U.S. Pat. No. 2,161,169 (Jefferis) there is disclosed a bone conduction hearing aid mounted in a denture. The denture includes at least one artificial incisor in which a microphone is mounted to receive sound and convert it to an electrical audio signal. That signal is transmitted by wire to a transducer located at the rear of the denture for converting the audio signal to mechanical vibrations that are conducted to the ear through the bone structure of the jaw. The transducer is covered by artificial molars in the denture, as is a battery employed to power the unit. This arrangement has a major disadvantage in that it only has utility for persons lacking at least one natural incisor and at least three natural molars. Moreover, in order to impart vibrations to the bone structure, the built-in transducer is provided with a diaphragm-mounted lug to impart vibrations to a denture wall which, in turn, is required to impart these vibrations to bones in the jaw. The denture wall must, therefore, be configured to provide a tight fit on the patient's gums, with the result that discomfort is likely. Moreover, as the gums automatically change, the required tight fit is compromised with the result that the vibrations are ultimately not efficiently transmitted to the bones in the jaw.

Another approach to hearing augmentation is disclosed in a series of patents to Puharich et al, namely U.S. Pat. Nos. 2,995,633, 3,156,787, 3,170,993 and 3,267,931. The devices and techniques described in these patents utilize a microphone-transmitter worn by the subject and arranged to convert sound to an audio-modulated radio frequency signal that is transmitted to a radio receiver in the subject's mouth. The receiver, which recovers the audio modulation, must be located adjacent a vital (i.e., live) tooth, or under a cap or filling of that vital tooth. The recovered audio signal is electrically coupled to the Facial Nerve (i.e., cranial Nerve VII) or the Trigeminal Nerve (i.e., Cranial Nerve V) in the tooth itself. It is the electrical transmission of the audio signal to and through this specific nerve network that is said to result in augmented hearing. In this regard, Puharich et al expressly state that the sensation of hearing does not result if vibrations are electrically insulated from the nerves, and that bone conduction of vibrations, of itself, is of very limited value as an aid to hearing using their apparatus and technique. Among the problems associated with the Puharich et al approach is the fact that the requirement for electrical coupling of the audio signal to the nerve network renders the system anatomically and physiologically difficult to implant and apply voltage without causing pain. It is also subject to failure by short circuits from leakage of saliva, and the like, as the fillings will be loosened by the underlying crystals. In addition, the Puharich et al approach requires that at least two of the subject's teeth be crowned, capped or otherwise treated to house the system components. Finally, it has been my observation in direct contradiction to Puharich et al, that transmission of the electrical audio signal via the Facial Nerve network of the patient is not nearly as efficient as bone-transmission of mechanical vibrations, if the mechanical vibrations are applied in the proper direction with sufficient voltage.

OBJECTS AND SUMMARY OF THE INVENTION

It is an object of the present invention to provide a method and apparatus for effecting reliable audiodontic hearing augmentation via bone conduction of mechanical vibrations without the disadvantages and shortcomings described above.

It is another object of the present invention to provide a method and apparatus for imparting mechanical vibrations to an endodontically treated dead tooth so that the vibrations maybe efficiently transmitted via bone to the ear.

The present invention is based in part on the recognition that teeth, particularly maxillary teeth, optimally transmit acoustic frequency vibrations to the inner ear. This is believed to result from: (1) the fact that the maxilla is made up of soft cancellous bone that transmits vibratory energy quite efficiently; (2) the fact that the maxilla has a large sinus cavity located immediately above the roots of the maxillary teeth; and (3) the fact that the teeth are secured to bone by ligaments, namely periodontal ligaments. It is noted that among and between all the bones of the human skull only the bones of the middle ear, the mandible, and the teeth are suspended by ligaments, as all others are rigidly sutured together.

It is clear, given the middle ear anatomy, that it is the ligaments joining the middle ear bones which permit the bones to vibrate in response to low or little sound pressure energy levels. The teeth, similarly suspended by ligaments, can be vibrated at relatively low energy levels, if the forces are directed in the proper direction. As an example, if a tuning fork is firmly held against the long axis of a tooth, its mechanical energy is transferred to the tooth, and its vibrations are perceived by the cochlea as a tone. The same tone would be similarly perceived if the vibrating tuning fork is held outside the ear, and the middle ear transduces the air sound pressure to vibrations for the cochlea. It is interesting that the same tuning fork produces the same tone at about the same loudness, thereby implying that the transducers are about equal.

In accordance with one embodiment of the present invention, a microphone-transmitter worn or carried by the subject, converts ambient sound to an audio-modulated radio signal. A dental implant for a tooth (preferably, but not necessarily a maxillary tooth) has a transducer embedded therein in order to impart vibrations to the tooth in response to applied electrical audio signals. In particular, the dental implant preferably takes the form of a post and core implanted in the root canal of the tooth, the post being a transducer of the piezo-electric or other suitable type which produces vibrations corresponding to applied electrical audio signals. Electrical lead wires or other conductors extend from the transducer dental post to transducer terminals at the core exterior. An electrically non-conductive crown covers the post and core and has a female electrical connector, made of gold or similar noble electrically conductive metal, embedded in its exterior. The contacts of the female connector are in electrical communication with respective transducer terminals located on the post and core periphery. Electrical audio signals are applied to the female connector from a male connector that engages the female connector in a precision fitting, the audio signals being conducted through to the transducer to produce the vibrations that are imparted to the tooth, then to bone in the jaw, and ultimately to the cochlea.

The male connector extends from a housing in which a radio receiver is disposed to recover the audio modulation appearing on received radio frequency signals, the recovered audio modulation being applied to the transducer through the connectors. The receiver housing is configured to reside in the subject's buccal or lingual vestibule or on the palate adjacent the tooth containing the implanted transducer. The female connector takes the form of a longitudinal recess or channel having a generally C-shaped cross-section and open at its upper end. Two conductive halves of the connector are separated by an insulative barrier or strip. The male connector has a matching periphery and cross-section permitting it to be slidably received in the open end of the female connector channel so that the male connector may be firmly held in place to provide both electrical connection as well as support for the receiver housing.

In an alternative embodiment of the invention, the subject wears a microphone to transduce ambient sound to an audio signal that is applied to a primary coil or winding typically worn about the subject's neck. The primary coil generates an electromagnetic field that varies in strength with the audio signal. A secondary or induction coil is housed in a denture or retainer disposed in the subject's mouth. The secondary coil is oriented so that a voltage is induced therein by the electromagnetic field generated by the primary coil. The length and orientation of the coil are also selected so that the level of the induced voltage is sufficient to excite a piezo-electric transducer, or the like, embedded in an endodontically treated tooth in the manner described above. The male connector in this embodiment is part of the denture or retainer housing the induction coil. This embodiment eliminates the need for demodulation circuitry in the subject's mouth.

BRIEF DESCRIPTION OF THE DRAWINGS

These and other objects, features and many of the attendant advantages of the present invention will be appreciated more readily as they become better understood from the reading of the following description considered in connection with the accompanying drawings wherein like parts in each of the several figures are identified by the same reference numerals, and wherein:

FIG. 1 is an exploded view in perspective showing a first embodiment of the present invention disposed in an endodontically treated mandibular tooth;

FIG. 2 is a view in perspective of the embodiment of FIG. 1 with the components fully assembled on the endodontically treated tooth;

FIG. 3 is a view in section taken along lines 3—3 of FIG. 2 with the male connector removed;

FIG. 4 is a view in perspective of the present invention employed in a maxillary tooth;

FIG. 5 is a plan view of another embodiment of the present invention wherein the receiver is housed in a denture;

FIG. 6 is a broken detailed view in perspective of a male connector employed in the embodiment of FIGS. 4 and 5;

FIG. 7 is a electrical schematic diagram of the system of FIGS. 1-4; and

FIG. 8 is an electrical schematic diagram of the system of FIGS. 5 and 6.

DESCRIPTION OF THE PREFERRED EMBODIMENTS

Referring specifically to FIGS. 1-3 of the accompanying drawings, an endodontically treated tooth includes a non-vital tooth portion 10 having a root canal 11 in which a dental post hole 13 is drilled. A typical core build-up 14 is made of an electrically non-conducting material such as a standard composite or acrylic. Post hole 13 is a diametrically widened section of the root canal 11 and filled with cement or insulation around transducer post 15 described below. The portion of the root canal 11 that does not contain the post is not widened and filled with a suitable dental filler material 17 such as gutta percha.

Embedded in post hole 13 by friction fit is an elongated transducer post 15 responsive to electrical signals in the audio frequency range applied to its terminals 15a and 15b for producing corresponding mechanical vibrations that are imparted to the surrounding structure of tooth 10. Transducer 15, in the preferred embodiment, is a piezo-electric ceramic having two separate electrical leads extending from respective terminals 15a, 15b to a terminal pad 20 secured by composite, or the like, at the core periphery.

Post 15 may be implanted in any one or more of the root canals of tooth 10. Further, as part of the implantation process, the selected canal can be widened as desired, and the depth of the transducer post 15 in the canal may be selected as desired. In this respect, the root canal 11 serves as an acoustic chamber and its dimensions may be chosen to enhance resonance for certain frequency ranges. By way of example only, if transducer post 15 is mounted in a palatal root canal, the canal can be widened to a diameter of three to five millimeters and the post can be inserted to a depth of ten to eleven millimeters. A crown 23 for tooth 10 is made of electrically non-conductive material, such as porcelain, acrylic, etc. Crown 23 is molded to fit over core 14 and is secured to tooth 10 by composites or other cements having insulative properties. A female connector 25 is embedded in an accessible surface of crown 23. This location is a non-bearing surface and is, therefore, subject to minimal adverse effects from occlusion, mastication, grinding, etc. Female connector 25 is configured to fit within the natural contour of the crown periphery and takes the form of two vertically elongated electrical contacts 25a, 25b separated by a vertically elongated insulating strip 26. More specifically, contacts 25a and 25b are elongated in the length dimension of tooth 10 and have generally J-shaped transverse cross-sections. Insulating strip 26 is bonded or adhesively secured to and between the longer ends of the J-shapes so that the overall transverse cross-section of the connector is generally C-shaped, thereby defining an elongated channel that is open at the edge of the crest surface of crown 23. Alternatively, the two contacts 25a, 25b may be separate members mounted in the crown recess and spaced by air or by crown material. In either case, the shorter legs of connector contacts 25a, 25b have their ends transversely spaced from one another by a distance that is less than the maximum transverse width of the connector channel to provide overhanging lips 29a, 29b for that channel. Contacts 25a, 25b are made from an electrically conductive metal (e.g., silver, gold, etc.) and are firmly secured to crown 23 in a position to contact respective interior terminals or core 14 at terminal pad 20. In order to effect this connection, contacts 25a, 25b may include respective rearward projections 27a, 27b disposed in direct contact with the terminals at pad 20.

A male connector 30 is adapted to be slidably engaged in female connector 25 through the open end of the female connector channel. Specifically, the transverse cross-section and periphery of connector 30 are configured with oppositely extending flanges 31a, 31b that fill the C-shaped channel defined in female connector 25 when the two connectors are engaged. Overhanging lips 29a, 29b of the female connector 25 serve to prevent the male connector 30 from being inadvertently disengaged from the female connector through the longitudinal channel opening. The engagement of male connector 30 in the channel is preferably secured by a precise friction fit that may be supplemented by a suitable dental adhesive. Connector 30 is made of an acrylic or other non-conductive material and typically projects from a housing for electrical components (not shown in FIGS. 1-3). Accordingly, electrical leads 33a, 33b extend from the electrical components through stem portion of male connector 30 to respective locations on flanges 31a and 31b where the leads communicate with respective contacts 25a, 25b of female connector 25.

As described in more detail below, the housing from which leads 33a, 33b extend contains a radio receiver that operates in conjunction with a microphone/transmitter that is worn or carried by the person or subject whose tooth 10 has been endodontically treated. The microphone/transmitter responds to ambient sound by providing a radio frequency signal that is modulated by that sound. The receiver, mounted in the mouth of the subject, receives the modulated radio signal and recovers the modulation as an electrical audio signal that is applied to leads 33a, 33b. This audio signal is applied to the contacts 25a, 25b of female connector 25 and then to transducer 15 via leads 19, 21. The transducer responds to the electrical audio signal by producing corresponding vibrations within the post hole 13, which vibrations are mechanically transmitted through tooth 10 to the mandible or maxilla, depending upon whether tooth 10 is a mandibular or maxillary molar, and ultimately to the cochlea.

Connection of leads 33a, 33b to contacts 25a, 25b, respectively, of female connector 25 may be effected by appropriate nubs (not illustrated) formed at the distal surface of flanges 31a, 31b. Alternatively, corresponding metal conductive strips may be provided at these distal surfaces of flanges 31a, 31b as terminations for leads 31a, 31b so that communication with respective contacts 25a and 25b may be provided along most of the length of those contacts.

Although the tooth 10 illustrated in FIGS. 1-3 is illustrated as extending upwardly, it is understood that this drawing orientation is arbitrary, and that tooth 10 may be either a mandibular or maxillary tooth. In the embodiment illustrated in FIG. 4, the endodontically treated molar is clearly a maxillary molar, and the male connector 30 is shown extending from housing 40 for a radio receiver. The housing 40 is molded acrylic or similar non-conductive material in which the receiver components are embedded and is contoured to comfortably reside in the buccal vestibule of the subject adjacent the endodontically treated tooth 10. As noted above, the cancellous nature of the maxilla, combined with the sinus cavity located therein, renders the present invention more advantageously employed in a maxillary tooth than in any other tooth. However, relatively efficient transmission of vibrations is nevertheless effected through mandibular teeth if these teeth are the only ones available for the endodontic treatment required to embody the present invention. In either case, the periodontal ligament connecting the tooth to either the maxilla or mandible permits efficient transmission of the vibrations produced in the tooth by means of the present invention.

Referring to FIGS. 5 and 6 of the accompanying drawings, an alternative embodiment of the invention includes a denture or palatal retainer 50 anchored in two locations. One location is at the endodontically treated tooth by means of connector 30 secured to the denture and connector 25 in crown 23. The other location is a conventional denture or orthodontic wire clasp 51 secured to one or more teeth on the opposite side of the subject's palate. The denture or retainer 50, in this embodiment, may house a receiver of the type described above to receive and demodulate a radio signal. As illustrated in FIG. 5, however, the denture/retainer may house a simple induction loop coil 57. For this latter embodiment the subject wears or carries a microphone that is connected to a primary coil or winding typically worn around the subject's neck. The primary coil creates an electromagnetic field to which induction coil 57 is oriented substantially perpendicular so that the field induces a voltage corresponding to the audio signal in the induction coil 57. The induced voltage is applied by means of electrical leads 53, 55 and through connectors 25, 30 to the transducer post 15 to impart mechanical vibrations to the tooth. This embodiment employs electromagnetic induction, rather than radio signals, to transmit the audio signal from the microphone pick-up to the tooth.

Referring now to FIG. 7 of the accompanying drawings, a microphone/transmitter 70 is typically worn or carried by the subject and includes a microphone responsive to ambient sound to provide a corresponding electrical signal. A transmitter housed in unit 70 transmits a signal at a predetermined radio carrier frequency, the radio signal being modulated by the audio signal sensed by the microphone. The receiver located in the subject's mouth, such as in housing 40 of FIG. 4 (or in a retainer or denture 53 of the type illustrated in FIG. 5), is tuned to the predetermined radio carrier frequency transmitted by microphone/transmitter 70 and, in a conventional manner, demodulates the received signal to recover the original audio signal derived by the microphone. The level of the audio signal may be varied by a potentiometer 73 that is also located in the housing and preset at the time housing 40 is molded about the receiver components. The level-adjusted audio signal is then applied to the male connector 30, the female connector 25 and, ultimately, to transducer 15 implanted in the subject's tooth. The required power supply (not shown) for the receiver/demodulator 71 is also contained within housing 40.

Referring to FIG. 8 of the accompanying drawings, the embodiment described in relation to FIGS. 5 and 6 includes a microphone 80 typically worn or carried by the subject. The audio signal provided by microphone 80 in response to ambient sound is applied across a primary coil 81 that is also worn or carried by the subject. Typically, as with prior art ear-mounted hearing aid systems using an electromagnetic field to transmit the audio signal, coil 81 is worn about the subject's neck. The induction coil 57 disposed in retainer/denture 50 (FIG. 5) serves as a secondary winding in which an audio signal is induced from the field generated by primary winding 81. The induced audio signal is applied via connectors 25, 30 to the transducer 15 embedded in the tooth. It is preferred that induction coil 57 take the form of a single coil having a length sufficient to cause the amplitude of the induced voltage to actuate transducer 15. If necessary, coil 57 may be oriented in plural turns or supplemented with an amplifier to achieve the desired amplitude. If an amplifier is employed, a power supply (i.e., a battery) must also be provided in denture/retainer 50.

The microphone/transmitter 70 may include two microphones worn appropriately by the subject in order to provide the benefit of binaural hearing. The two resulting sound signals may be separately modulated on independent radio signals of different frequency or in respective side bands of the same radio frequency signal. In either case, the one or two radio signals are demodulated in the receiver located in the mouth of the subject, and the two recovered audio signals are applied to two separate transducers in two or more respective endodontically treated root canals located in different parts of the subject's mouth. In this manner the two resulting vibratory signals are transmitted through the maxilla or mandible bone structure to respective cochlea and, because of the varying transmission rates of each implanted transducer to a corresponding ear, the vibrations are interpreted at the respective cochlea in a manner similar to that in which the ear binaurally interprets sound received via air conduction. Also, proprioceptor nerve fibers located in the periodontal ligaments of the tooth or teeth may help the subject perceive the spacial orientation of binaural hearing.

An important aspect of the present invention resides in the fact that the dental implant hearing aid is located inside a tooth, or dental implant not really inside the bones of the maxilla or mandible. In other words, the implanted device does not touch or communicate with blood or body fluids. Consequently, the risk of infection is insignificant as compared to hearing aid implants that are intended to integrate with bone structure or other bodily tissue.

From the foregoing description it will be appreciated that the invention makes available a novel method and apparatus wherein an endodontically implanted transducer, in a single tooth, is capable of providing sound related vibrations that are efficiently transmitted by bone to a subject's cochlea to thereby significantly augment the subject's hearing capacity.

Having described preferred embodiments of a new and improved method and apparatus for endodontically augmenting hearing in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. Apparatus for aiding hearing by imparting vibrations to bones in a jaw of a subject, said apparatus comprising:
    transducer means adapted to be embedded in a root canal of a tooth of the subject and responsive to application of electrical audio driver signals thereto for imparting corresponding vibratory signals to said bones via said tooth, said transducer means having a plurality of electrical transducer terminals;
    a dental crown disposed on said tooth covering said transducer means and said transducer terminals; and
    first and second connectors, said first connector being secured to said crown and including a plurality of crown contacts in electrical connection with said plurality of transducer terminals, respectively, said second connector including contact means for delivering said audio driver signals to said plurality of crown contacts when said connectors are engaged.

2. The apparatus according to claim 1 further comprising:
    radio receiver means for receiving a radio signal modulated by audio signals and demodulating the received signal to provide said audio driver signals;
    a housing for said radio receiver means contoured to be positioned in the mouth of said subject, said housing having said second connector secured thereto to provide the recovered audio signals exteriorly of said housing.

3. The apparatus according to claim 2 wherein said housing is configured to fit into the buccal vestibule of said subject adjacent said tooth, and wherein said receiver means is embedded in said housing along with electrical conductors extending from said receiver means to said second connector.

4. The apparatus according to claim 2 wherein said housing is a removable partial denture or orthodontic retainer configured to fit adjacent the subject's palate.

5. The apparatus according to claim 2 wherein said crown is electrically non-conductive, and wherein one of said first and second connectors is a female connector, the other of said first and second connectors being a male connector adapted to be received in and engaged by said female connector in secure electrical contact while supporting said housing.

6. The apparatus according to claim 5 wherein said female connector comprises first and second electrically conductive sections extending longitudinally and electrically insulated in transversely spaced relation by a longitudinally-extending electrically-insulating section, said female connector having a longitudinally-extending channel defined therein with a predetermined transverse cross-section and open at one end;

and wherein said male connector comprises a projection adapted to be slidably received in said channel through said open one end, said projection having a transverse cross-section corresponding to said predetermined transverse cross-section such that said projection, when slidably inserted into said channel, is held securely therein, said projection including first and second contacts corresponding to said contact means and positioned to electrically contact said first and second sections, respectively, when said projection is slidably received in said channel.

7. The apparatus according to claim 6 wherein said predetermined transverse cross-section is generally C-shaped such that said channel has a longitudinally-extending opening of shorter transverse width than the transverse width of said channel at its widest part, and wherein said male connector includes a stem portion extending out of said channel through said opening when the male and female connectors are engaged.

8. The apparatus according to claim 7 wherein said female connector is embedded in said crown and wherein said male connector is a structural part of said housing.

9. The apparatus according to claim 8 wherein said tooth is a maxillary tooth, and wherein said female connector is disposed at the buccal surface of said crown.

10. The apparatus according to claim 9 wherein said female connector is said first connector and is recessed in said crown to subsist within the external contour of the crown.

11. The apparatus according to claim 10 wherein said tooth is a maxillary tooth, and wherein said female connector is disposed at the buccal surface of said crown.

12. The apparatus according to claim 5 wherein said female connector comprises a body having a longitudinally-extending channel defined therein with a predetermined transverse cross-section and open at one end;
wherein said male connector comprises a projection from said housing adapted to be slidably received through said open one end, said projection having a transverse cross-section corresponding to said predetermined transverse cross-section of said channel such that said projection, when slidably inserted to said channel is held securely therein;
wherein said female connector includes first and second electrically-isolated contacts exposed in said channel;
and wherein said male connector includes first and second terminals corresponding to said contact means and positioned to electrically contact said first and second contacts of said female connector when said male connector is engaged in said female connector.

13. The apparatus according to claim 5 wherein said transducer means is a piezo-electric transducer having first and second terminals extending longitudinally into said root canal.

14. The apparatus according to claim 5 wherein said female connector is said first connector and is recessed in said crown to subsist within the external contour of the crown.

15. The apparatus according to claim 1 further comprising:
induction coil means, responsive to being disposed in an electromagnetic field having a strength that varies with the amplitude of primary audio signals, for providing said audio driver signals as induced audio signals that vary in proportion to the primary audio signals;
a housing for said induction coil means contoured to be disposed in the mouth of said subject, said housing having said second connector secured thereto to provide the induced audio signals exteriorly of said housing.

16. The apparatus according to claim 15 wherein said housing is a removable partial denture or orthodontic retainer configured to fit adjacent the subject's palate.

17. A method of enhancing conduction of sound to an ear of a subject via bone tissue in a jaw of the subject, said method comprising the steps of:
(a) converting audible ambient sound to corresponding acoustic signals;
(b) transmitting said acoustic signals through a non-conductive crown and core of a maxillary tooth of said subject to the root canal of said tooth;
(c) transducing the audio signal in said root canal to a corresponding vibratory signal; and
(d) applying said vibratory signal from the root canal to bones in the maxilla or mandible of said subject to permit transmission of the vibratory signal to the subject's cochlea.

18. The method of implanting a hearing enhancement device in a tooth comprising the steps of:
(a) implanting in the root canal of said tooth a transducer dental post for converting electrical audio signals to corresponding mechanical vibrations;
(b) building a non-conductive dental core around and attached to said transducer post;
(c) disposing first and second electrical conductors within said core extending from respective first and second terminals of said transducer to predetermined respective first and second spaced locations at the exterior of said core;
(d) securing a first electrical connector, having first and second electrically-isolated crown contacts, to an artificial electrically non-conductive crown for said tooth;
(e) seating said crown on said core and transducer post in a position such that said first and second crown contacts electrically connect to said first and second conductors, respectively, at said first and second locations; and (f) mating said first connector in a precision fit with a second connector at the exterior of said crown to permit electrical audio signals to be applied via said connectors to said first and second crown contacts of said first connector.

19. The method according to claim 18 further comprising the steps of:
 (g) forming a housing of electrically non-conducting material in a size and shape to fit in a patient's buccal or lingual vestibule adjacent said tooth with the second connector forming a structural part of said housing;
 (h) embedding in said housing a radio receiver for receiving selected radio signals and demodulating the selected radio signals to recover modulating audio signals therefrom; and
 (i) embedding in said housing third and fourth electrical conductors carrying said recovered audio signals from said radio receiver to respective locations of said second connector that contacts said first and second crown contacts, respectively of said first connector;
 whereby said first and second connectors, when mated, support said housing in said buccal vestibule.

20. The method according to claim 18 further comprising:
 (g) forming a removable partial denture or orthodontic retainer having embedded therein means for providing recovered audio signals such that said second connector is a part of said partial denture or retainer; and
 (h) embedding in said partial denture third and fourth electrical conductors carrying said recovered audio signals from said means to respective locations of said second connector that contact said first and second crown contacts, respectively, of said first connector.

21. Apparatus for aiding hearing by imparting vibrations to bones in a jaw of a person, said apparatus comprising:
 microphone/transmitter means adapted to be worn or carried by said person and responsive to ambient sound for transmitting a radio signal modulated as a function of said ambient sound;
 a palatal orthodontic retainer adapted to be secured in the person's mouth adjacent the person's palate, said retainer housing a receiver for receiving and demodulating said radio signal to recover an electrical signal corresponding to said ambient sound; and
 transducer means responsive to said electrical signal for imparting vibrations corresponding to said ambient sound to said bones via a tooth in said person's mouth.

* * * * *